(12) United States Patent
Wu et al.

(10) Patent No.: US 7,820,689 B2
(45) Date of Patent: Oct. 26, 2010

(54) METHODS AND COMPOSITIONS FOR PREVENTING OR TREATING CARDIOVASCULAR DISEASE

(76) Inventors: Hua-Lin Wu, No. 1, University Rd., Tainan 701 (TW); Guey-Yueh Shi, No. 1, University Rd., Tainan 701 (TW)

( * ) Notice: Subject to any disclaimer, the term of this patent is extended or adjusted under 35 U.S.C. 154(b) by 0 days.

(21) Appl. No.: 11/836,159

(22) Filed: Aug. 9, 2007

(65) Prior Publication Data

US 2008/0039484 A1 Feb. 14, 2008

Related U.S. Application Data

(60) Provisional application No. 60/822,070, filed on Aug. 10, 2006.

(51) Int. Cl.
*A61K 31/44* (2006.01)
*A61K 38/00* (2006.01)
(52) U.S. Cl. .............................. 514/282; 514/18; 514/19
(58) Field of Classification Search .................. 514/282
See application file for complete search history.

(56) References Cited

U.S. PATENT DOCUMENTS 6,403,830 B2 * 6/2002 Webber et al. .............. 562/557

| | | | |
|---|---|---|---|
| 2002/0169159 A1 * | 11/2002 | Medina et al. | 514/227.5 |
| 2004/0063628 A1 * | 4/2004 | Piccariello et al. | 514/12 |
| 2005/0107415 A1 * | 5/2005 | Wu et al. | 514/282 |
| 2006/0069086 A1 | 3/2006 | Michalow | |
| 2006/0111272 A1 * | 5/2006 | Roberts et al. | 514/2 |
| 2006/0167075 A1 * | 7/2006 | Pearson et al. | 514/406 |
| 2008/0045610 A1 | 2/2008 | Michalow | |

OTHER PUBLICATIONS

Moreno et al. (Macrophage infiltration predicts restenosis after coronary intervention in patients with unstable angina, Circulation, Dec. 15, 1996; 94(12): 3098-102, printed pp. 1 and 2, especially p. 1.*
Blackshear et al., Medical approaches to prevention of restenosis after coronary angioplasty, J Am Coll Cardiol, 1987; 9:834-848, printed pp. 1 and 2, especially p. 1.*
Raines, Cytokines affecting endothelial and smooth muscle cells in vascular disease; Journal of Lipid Research; Apr. 16, 2005, 2005, 46:1081-1092.
Ross, Russell. Atherosclerosis—An Inflammatory Disease. Mechanism of Disease. vol. 340, No. 2, Jan. 14, 1999.

* cited by examiner

*Primary Examiner*—Sreeni Padmanabhan
*Assistant Examiner*—Timothy E Betton
(74) *Attorney, Agent, or Firm*—WPAT, P.C.; Anthony King

(57) ABSTRACT

The present invention relates to a method for preventing or treating a cardiovascular disease.

13 Claims, 16 Drawing Sheets

A

B

A

B

C

A

B

A

Control    Naloxone

B

C

A

B

A

B

A

B

A

B

A

B

United States Patent US 7,820,689 B2

METHODS AND COMPOSITIONS FOR PREVENTING OR TREATING CARDIOVASCULAR DISEASE

FIELD OF THE INVENTION

The present invention relates to a method for preventing or treating a cardiovascular disease. The invention also relates to a method for preventing or treating atherosclerosis or the patient suffering restenosis.

BACKGROUND OF THE INVENTION

Dextromethorphan (DM, (+)-3-methoxy-17-methyl-9a,13a,14a-morphinan), a widely used over-the-counter antitussive agent, is a noncompetitive antagonist of the N-methyl-D-aspartate (NMDA) receptor and is protective against the adverse effect of homocysteine (Hcy) and its metabolites. DM, the D-isomer of the opiate agonist levorphanol, has none of the analgesic or sedative effects associated with the opiates. DM, acting as an antagonist at NMDA receptors, suppresses the transmission of nerve impulses and nerve signals mediated through NMDA receptors. In addition, DM has also been reported to suppress activity at neuronal calcium channels.

Naloxone (trade name Narcan) is a drug used to counter the effects of overdosing on opiates such as heroin or morphine. Naloxone has been distributed as part of emergency kits to heroine addicts, which has been shown to reduce death rates. The drug also blocks the action of pain-lowering endorphins which the body produces naturally. The likely reason for this is that these endorphins operate on the same opiate receptors.

Macrophages secrete numerous other effectors including reactive oxygen species, eicosanoids, tumour necrosis factor alpha (TNF-α), interleukin-1 (IL-1) and interleukin-6 (IL-6). Macrophage-derived transforming growth factor beta promotes fibrosis. Existing cardiovascular treatments including angiotensin II receptor antagonists and angiotensin converting enzyme inhibitors, aspirin, cholesterol reduction agents especially statins may inhibit macrophages. The interaction of NO-donors with macrophages and apoptosis is complex and bifunctional. Traditional anti-inflammatory agents such as glucocorticoids and cyclophosphamide have very serious side effects and are probably inappropriate.

Atherosclerosis remains a leading cause of morbidity and mortality worldwide. Central to the pathogenesis of atherosclerosis is the infiltration of monocytes/macrophages in the arterial wall and the involvement of inflammation. Macrophages play a diverse array of roles in atherogenesis. They functions as a scavenger cell that takes up oxidized low-density lipoprotein (oxLDL) and become foam cells in the initial lesion of atherosclerosis. After activation, macrophages are capable of producing free radicals and pro-inflammatory factors, all of which are critical for the promotion of cellular proliferation and inflammation in atherosclerosis. Evidence indicates that atherosclerotic lesions could be decreased if monocyte/macrophage extravasation and activation is inhibited (Gosling J, et al., J Clin Invest, 103:773-8, 1999). Naloxone is a non-selective antagonist of the opioid receptors that are widely expressed not only in the central nervous system but also on the endothelium and monocytes. Previous animal studies found that naloxone can significantly decrease the inflammatory response in septic shock. It inhibits the production of tumor necrosis factor-α (TNF-α) induced by lipopolyssacharide (LPS) in mice. Recent studies also show that naloxone reduces the pro-inflammatory factors and superoxide generation from LPS-induced microglia, the resident macrophages within the nervous system (Liu B, Hong J S., J Pharmacol Exp Ther, 304:1-7, 2003).

naloxone for 10 weeks. The results are expressed as mean±SD. P<0.01; *P<0.005 compared with the control.

Figure 8:
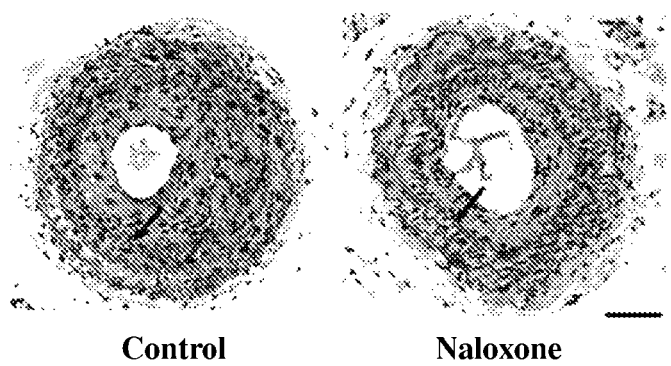
Figure 8:
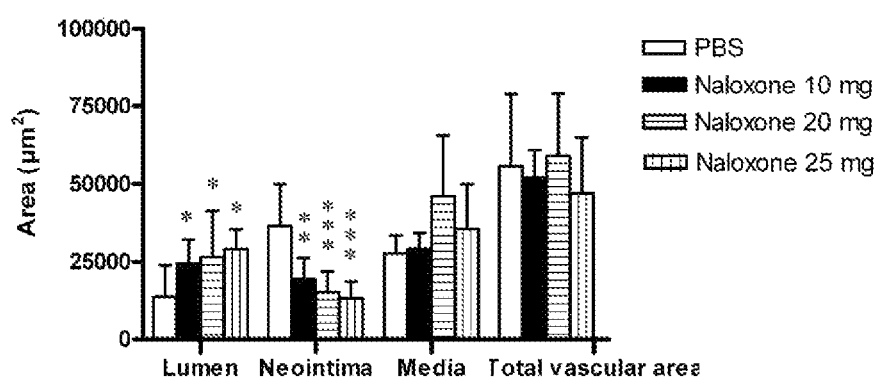
Figure 8:
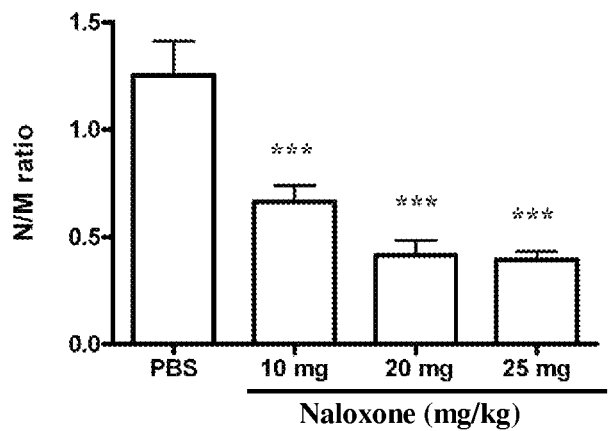

FIG. 8 shows representative photomicrographs of hematoxylin-eosin staining of arterial sections 28 days after carotid ligation in mice receiving naloxone (right panel) or PBS injection (left panel). Arrows indicate borders of the neointima and media. Original magnification is ×200. (A). Morphometric analysis of the lumen, neointima, media, and total vascular areas. Values are mean±SD of five sections in each mouse. *P<0.05; P<0.01; *P<0.005 compared with the mice receiving PBS injection (B). Degree of neointima formation 28 days after carotid ligation was calculated according to neointima/media area (N/M) ratio. ***P<0.005 compared with the mice receiving PBS injection (C). (bar=100 μm)

Figure 9:
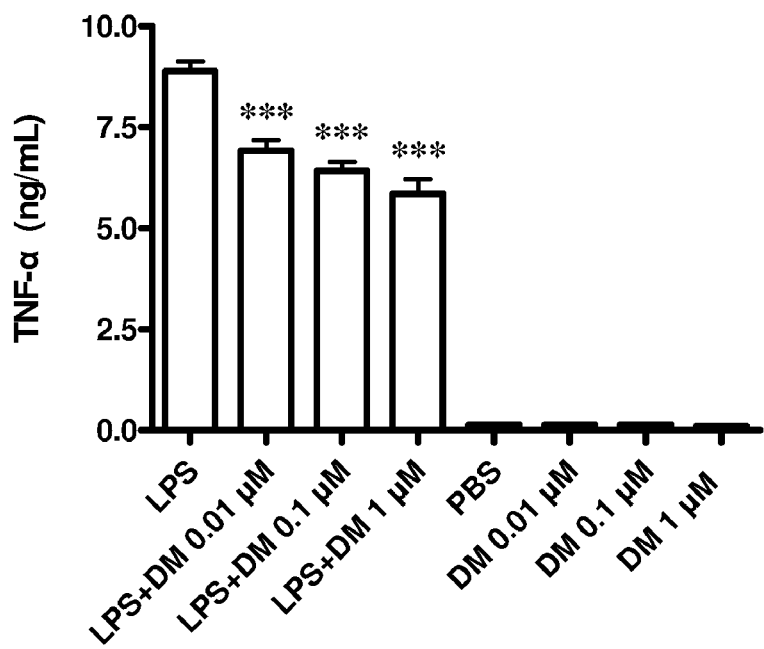
Figure 9:
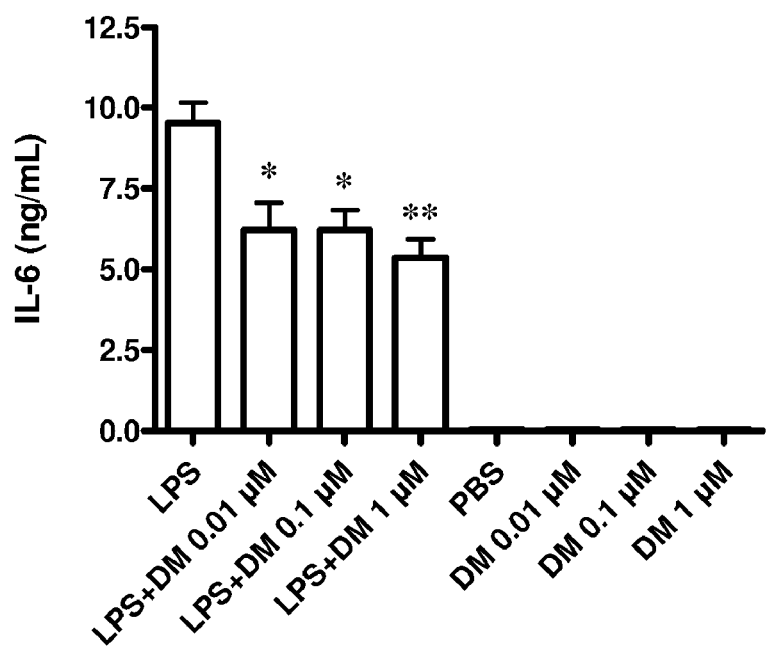

FIG. 9 shows effect of DM treatment on the LPS-induced macrophage release of TNF-α (A) and IL-6 (B). THP-1 cell culture was pretreated for 1 hour with the indicated concentrations of DM before stimulation with 100 ng/mL LPS. Supernatants were harvested at 24 hours for the measurement of TNF-α and IL-6. Data are expressed as mean±SD (n=9) of 3 independent experiments. *P<0.05; P<0.01; *P<0.001 compared with the LPS-treated cultures.

Figure 10:
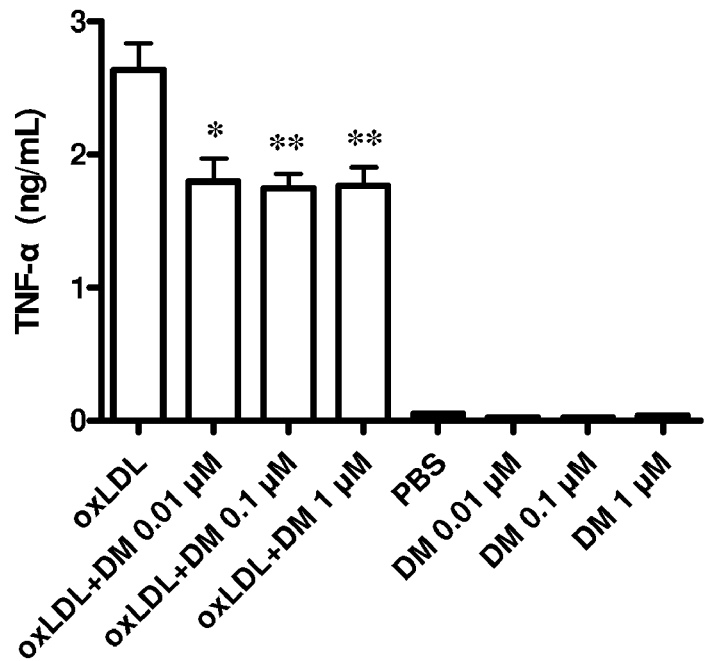
Figure 10:
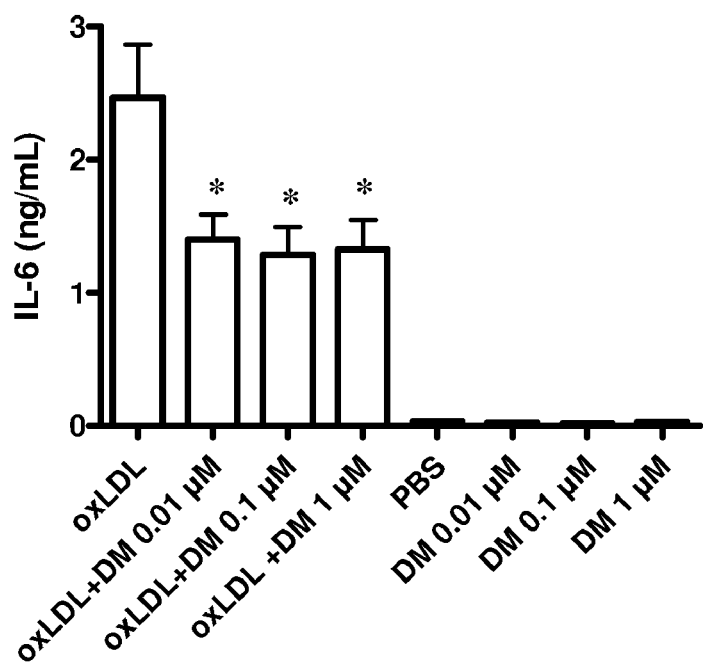

FIG. 10 shows effect of DM treatment on oxLDL-induced macrophage release of TNF-α (A) and IL-6 (B). THP-1 cell culture was pretreated for 1 hour with the indicated concentrations of DM before stimulation with 10 μg/mL oxLDL. Supernatants were harvested at 24 hours for the measurement of TNF-α and IL-6. Data are expressed as mean±SD (n=9) of 3 independent experiments. *P<0.05; **P<0.01 compared with the oxLDL-treated cultures.

Figure 11:
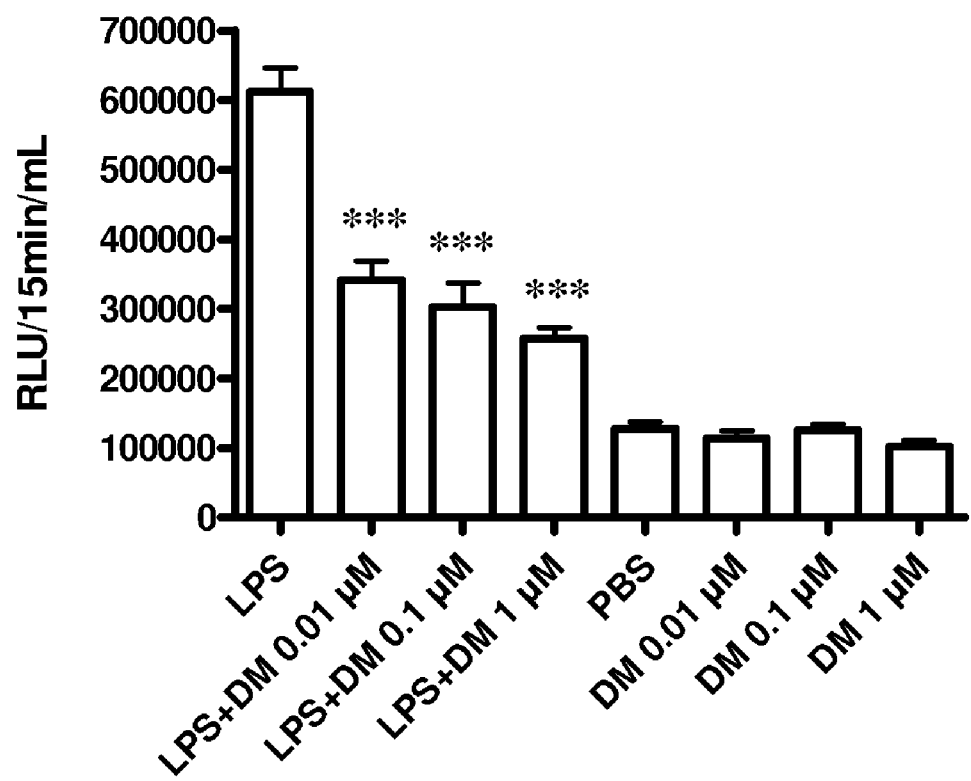

FIG. 11 shows effect of DM treatment on LPS-induced macrophage production of superoxide. THP-1 cell culture was pretreated for 1 hour with the indicated concentrations of DM before stimulation with 100 ng/mL LPS. Production of superoxide in THP-1 cell culture was measured by lucigenin-enhanced chemiluminescence. Data are expressed as mean±SD (n=9) of 3 independent experiments. ***P<0.001 compared with the LPS-treated cultures.

Figure 12:
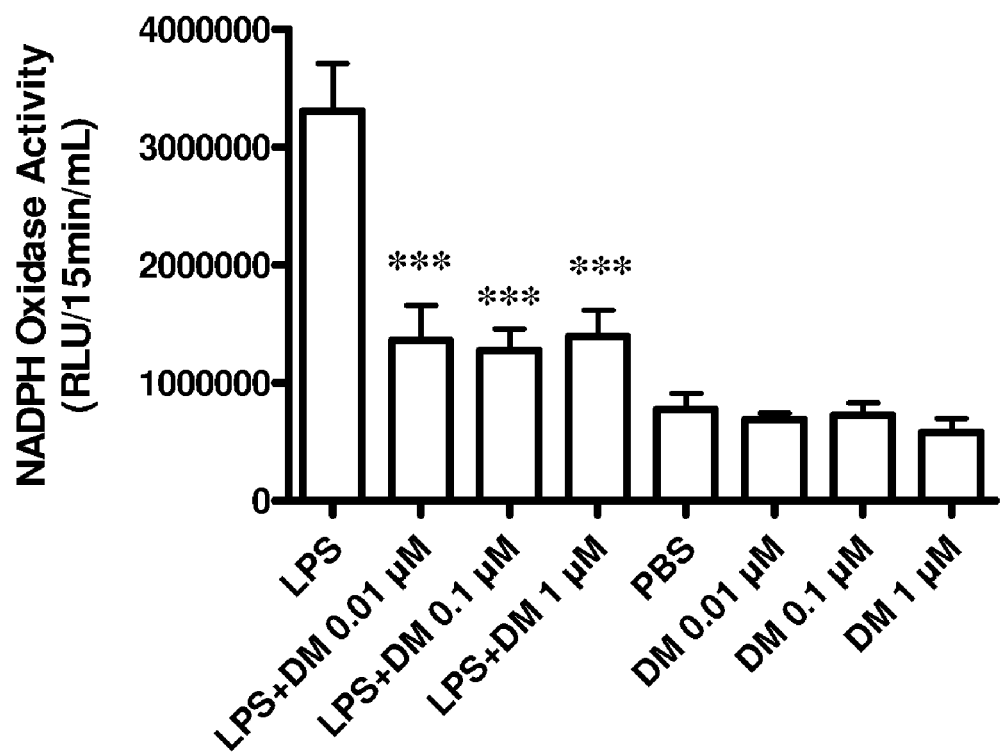

FIG. 12 shows influence of DM treatment on macrophage NADPH oxidase activity. THP-1 cell culture was pretreated for 1 hour with the indicated concentrations of DM before stimulation with 100 ng/mL LPS. Lysis buffer was added to the cells and centrifuged. The supernatant was discarded and the pellet was resuspended. NADPH oxidase activity was measured by mixing 30 μg protein, 5 μM lucigenin, and 100 μM NADPH. Chemiluminescence was determined every 10 seconds for 15 minutes. Data are presented as mean±SD (n=8-15). ***P<0.001 compared with the LPS-treated cells.

Figure 13:
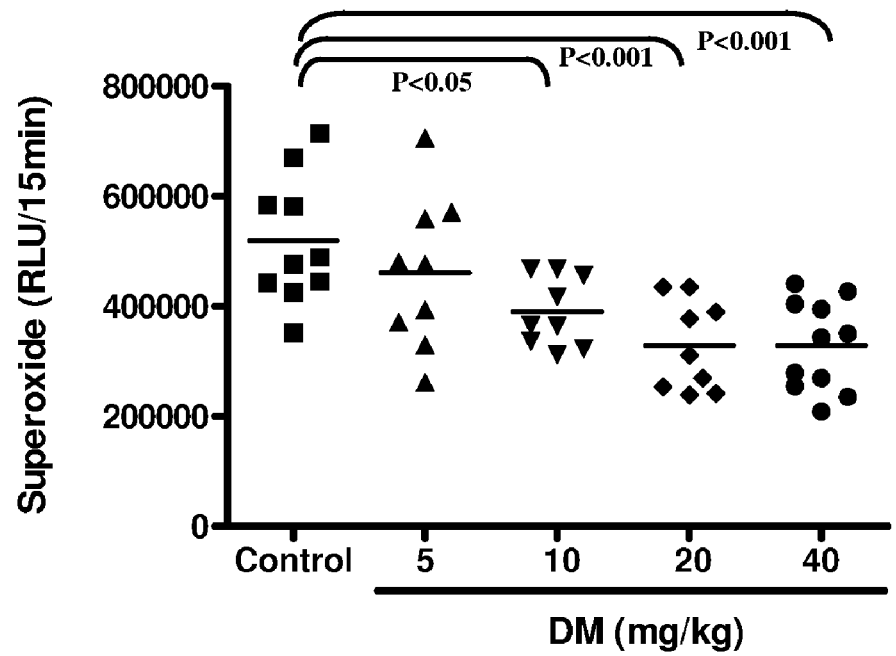
Figure 13:
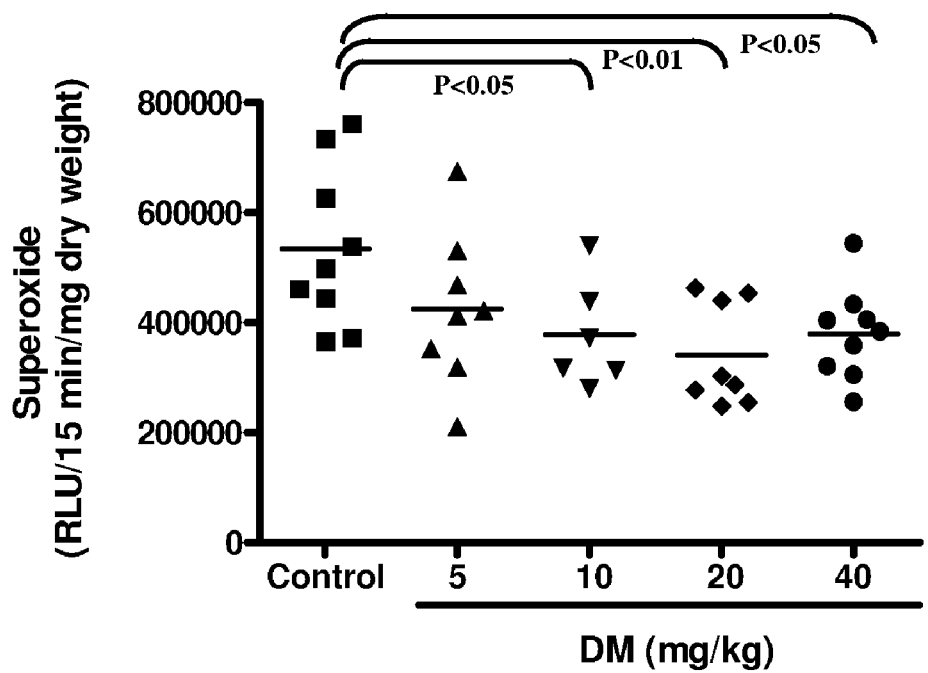

FIG. 13 shows influence of DM treatment on production of the superoxide anion in the PMN (A) and aorta (B) of apoE-deficient mice. ApoE-deficient mice were treated daily with DM 5 mg/kg/day (n=9), 10 mg/kg/day (n=9), 20 mg/kg/day (n=9) or 40 mg/kg/day (n=11) for 10 weeks. Production of superoxide in PMN ($1 \times 10^6$ cells/mL PBS) (A) was measured by lucigenin-enhanced chemiluminescence. The results are expressed as mean±SD. (P<0.05, control versus 10 mg/kg/day; P<0.001, control versus 20 mg/kg/day and 40 mg/kg/day). Production of superoxide in the thoracic aorta (B) was also measured by lucigenin-enhanced chemiluminescence. The results are expressed as mean±SD. (P<0.05, control versus 10 mg/kg/day and 40 mg/kg/day; P<0.01, control versus 20 mg/kg/day).

Figure 14:
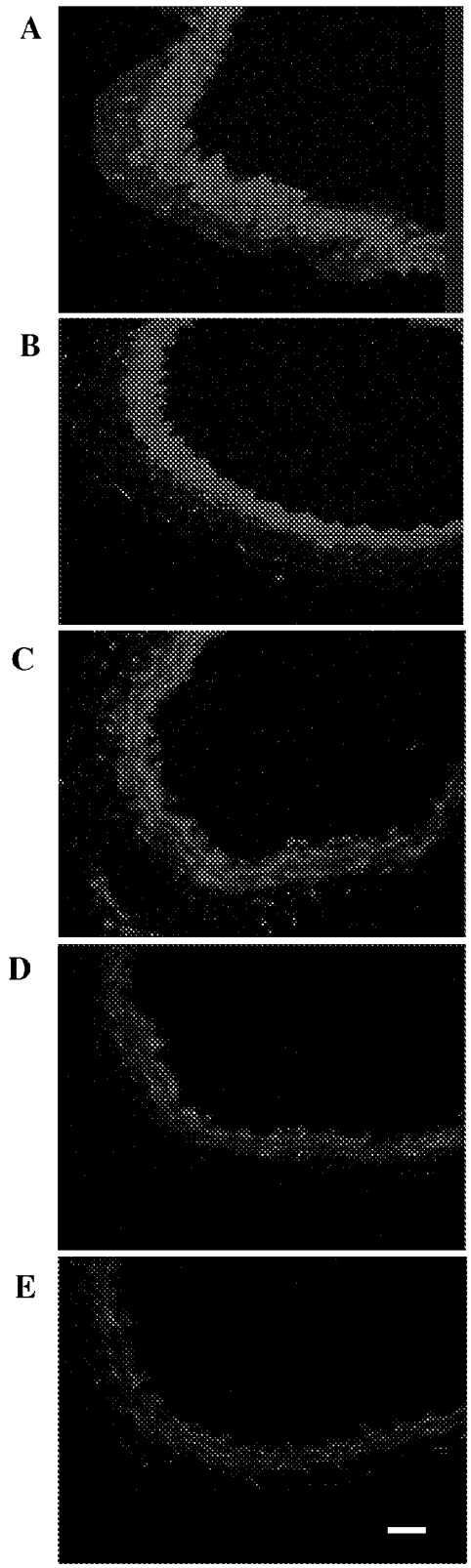

FIG. 14 shows superoxide formation in the mouse left common carotid artery evaluated by oxidative fluorescent microtopography with the oxidative fluorescent dye DHE. Representative photomicrographs of the aortic sections in apoE-deficient mice were treated daily with water only (A) or DM 5 mg/kg/day (B), 10 mg/kg/day (C), 20 mg/kg/day (D) or 40 mg/kg/day (E) for 10 weeks. In comparison, staining was much more reduced in the aorta of animals receiving DM pretreatment. The results are representative of 4 independent experiments with 6-8 independently analyzed mice/group. (bar=50 μm)

Figure 15:
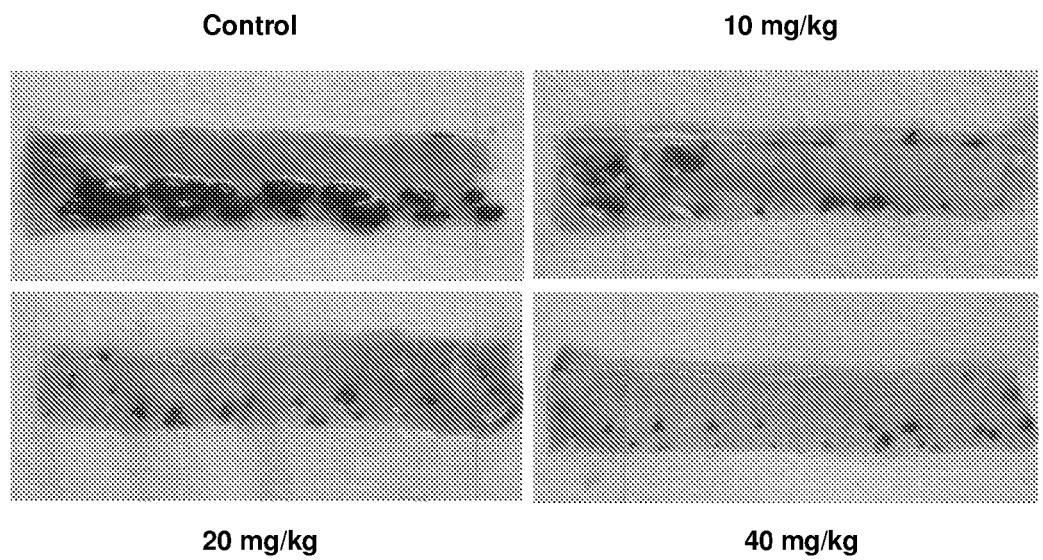
Figure 15:
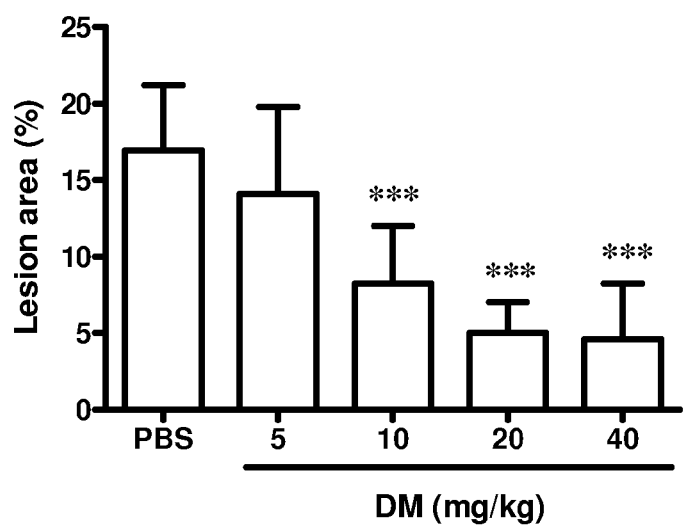

FIG. 15 shows influence of DM treatment on atherosclerotic lesion formation in apoE-deficient mice. The lipid-rich atherosclerotic lesions were identified with Oil-Red-O staining. Representative photomicrographs are shown (A). Lesion area (%) was expressed as percentage of atherosclerotic area/total area of the aorta (B). ApoE-deficient mice were treated daily with DM 5 mg/kg/day (n=10), 10 mg/kg/day (n=9), 20 mg/kg/day (n=9) or 40 mg/kg/day (n=9) for 10 weeks. The results are expressed as mean±SD. ***P<0.001 compared with the control.

Figure 16:
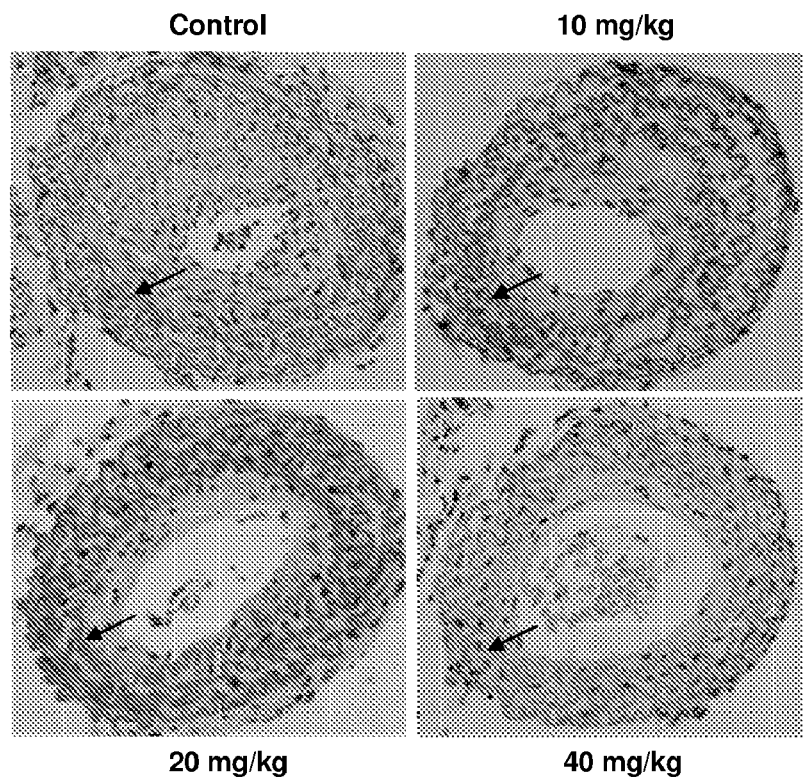
Figure 16:
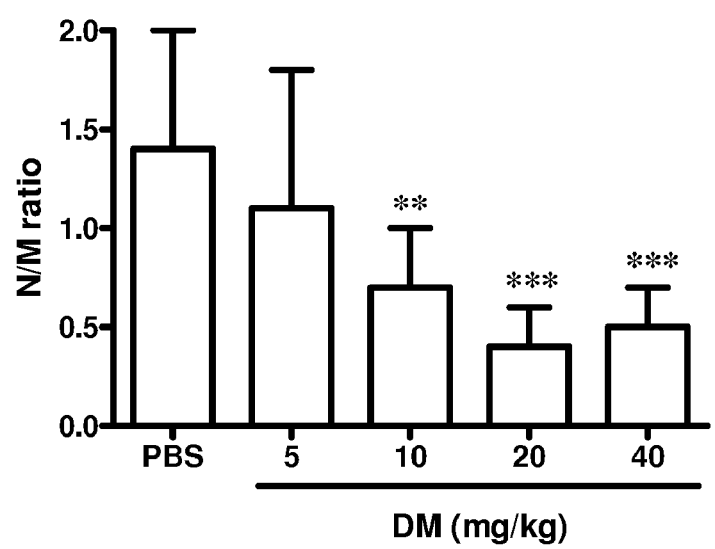

FIG. 16 shows representative photomicrographs of hematoxylin-eosin staining of arterial sections 28 days after carotid ligation in mice treated daily with DM 5 mg/kg/day (n=6), 10 mg/kg/day (n=7), 20 mg/kg/day (n=9) or 40 mg/kg/day (n=8) for 4 weeks. Arrows indicate borders of the neointima and media. Original magnification is ×200. (bar=100 μm) (A). Degree of neointima formation 28 days after carotid ligation was calculated according to N/M ratio. P<0.01; *P<0.001 compared with the mice receiving PBS injection (B).

SUMMARY OF THE INVENTION

The present invention provides a method for preventing or treating a cardiovascular disease comprising administering a patient in need of such treatment a therapeutically effective amount of a compound of formula I or formula II, or a pharmaceutically acceptable salt or an analog thereof.

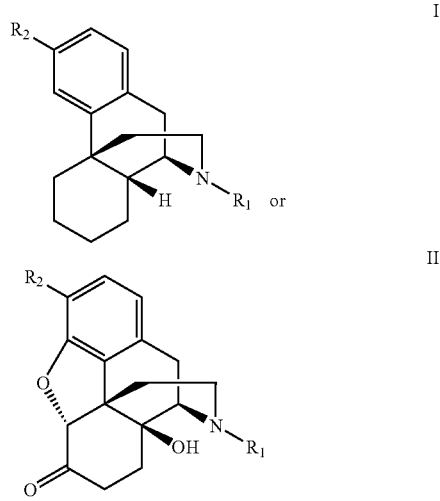

wherein $R_1$ is $C_{1-6}$ alkyl, $C_{2-6}$ alkenyl, cyclo$C_{3-6}$ alkyl-$C_{1-6}$ alkyl, or $C_{2-6}$ alkylene, and $R_2$ is H, OH, $C_{1-6}$ alkyl, $C_{1-6}$ alkoxy, $C_{2-6}$ alkenyl or $C_{2-6}$ alkylene.

DETAILED DESCRIPTION OF THE INVENTION

Accordingly, the present invention relates to a method for preventing or treating a cardiovascular disease comprising administering a patient in need of such treatment a therapeutically effective amount of a compound of formula I or formula II, or a pharmaceutically acceptable salt or an analog thereof

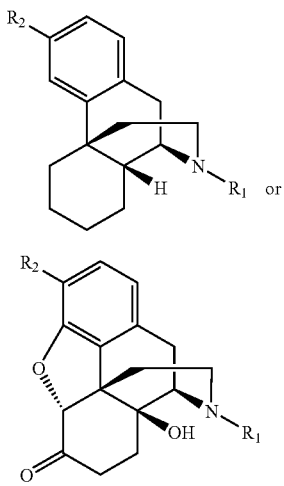

wherein $R_1$ is $C_{1-6}$ alkyl, $C_{2-6}$ alkenyl, cyclo$C_{3-6}$ alkyl-$C_{1-6}$ alkyl, or $C_{2-6}$ alkylene, and $R_2$ is H, OH, $C_{1-6}$ alkyl, $C_{1-6}$ alkoxy, $C_{2-6}$ alkenyl or $C_{2-6}$ alkylene.

The preferred compound of formula I is (+)-3-methoxy-17-methyl-9α,13α,14α-morphinan (dextromethorphan). The preferred salt of formula I is dextromethorphan hydrobromide or dextromethorphan phosphate. The preferred compound of formula II is 17-allyl-4,5α-epoxy-3,14-dihydroxymorphinan-6-one (naloxone) or 17-(cyclopropylmethyl)-4,5α-epoxy-3,14-dihydroxymorphinan-6-one (naltrexone). Most of the addictive analgesic opiates, such as morphine, codeine, and heroin, are levorotatory stereoisomers (they rotate polarized light in the so-called left-handed direction). They have four molecular rings in a configuration known as a "morphinan" structure. Many dextrorotatory analogs of morphine are much less addictive than the levorotatory compounds. Some of these dextrorotatory analogs, including dextromethorphan and dextrorphan, are enantiomers of the morphinan structure. In these enantiomers, the ring that extends out from carbon atoms 9 and 13 is oriented in the opposite direction from that depicted in the above structure.

A dose of the pharmaceutical composition contains at least a therapeutically effective amount of the active compound (i.e., a compound of formula I or a pharmaceutically acceptable salt thereof), and preferably is made up of one or more pharmaceutical dosage units. The selected dose may be administered to a mammal, for example, a human patient, in need of such treatment a therapeutically effective amount of a compound of formula I or a pharmaceutically acceptable salt or an analog thereof, by any known or suitable method of administering the dose, including topically, for example, as an ointment or cream; orally; rectally, for example, as a suppository; parenterally by injection; or continuously by intravaginal, intra-nasal, intra-bronchial, intra-aural, or intra-ocular infusion.

The terms "Cardiovascular disease" or "cardiovascular lesion" used herein refers to any of a variety of disease or lesions to the heart or vasculature of a subject. Examples include atherosclerosis (i.e. thickening and hardening of arteries due to plaque formation) and related disorders resulting from occluded blood flow (e.g. angina, cerebral ischemia, renal hypertension, ischemic heart disease, stroke) and thrombus and formation (e.g. Deep Vein Thrombosis (DVT)).

The term "therapeutically effective amount" is intended to mean the amount of an inventive compound that, when administered to a mammal in need thereof, is sufficient to effect prevention or treatment for disease conditions alleviated by the inhibition of the genesis of cardiovascular diseases. Such disease as atherosclerosis involves restenosis. In a preferred embodiment, the method of the present invention can prevent or treat in-stent restenosis. The amount of a given compound of the invention that will be therapeutically effective will vary depending upon factors such as the particular compound, the disease condition and the severity thereof, the identity of the mammal in need thereof, which amount may be routinely determined by artisans. The stent described by Palmaz in U.S. Pat. No. 4,733,665 can be used to repair an occluded blood vessel.

The term "pharmaceutically acceptable salt" used herein means any salt that is pharmaceutically acceptable and has the desired pharmacological properties. Such salts include salts that may be derived from an inorganic or organic acid, or an inorganic or organic base, including amino acids, which is not toxic or undesirable in anyway. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane and arene-sulfonic acids such as methanesulfonic acid, benzenesulfonic acid, sulfonic acid, and phosphatic acid). When there are two acidic groups present, a pharmaceutically acceptable salt may be a mono-acid-mono-salt or a di-salt; and similarly, where there are more than two acidic groups present, some or all of such groups can be salified.

The term "dyslipidemia" used herein means a disorder of lipoprotein metabolism, including lipoprotein overproduction or deficiency. Dyslipidemias may be manifested by elevation of the total cholesterol, the "bad" low-density lipoprotein (LDL) cholesterol and the triglyceride concentrations, and a decrease in the "good" high-density lipoprotein (HDL) cholesterol concentration in the blood. Dyslipidemia comes under consideration in many situations including diabetes, a common cause of lipidemia. For adults with diabetes, it has been recommended that the levels of LDL, HDL, and total cholesterol, and triglyceride be measured every year. Optimal LDL cholesterol levels for adults with diabetes are less than 100 mg/dL (2.60 mmol/L), optimal HDL cholesterol levels are equal to or greater than 40 mg/dL (1.02 mmol/L), and desirable triglyceride levels are less than 150 mg/dL (1.7 mmol/L).

The present invention provides a composition for preventing or treating a cardiovascular disease comprises a compound of formula I or formula II, or a pharmaceutically acceptable salt or an analog thereof

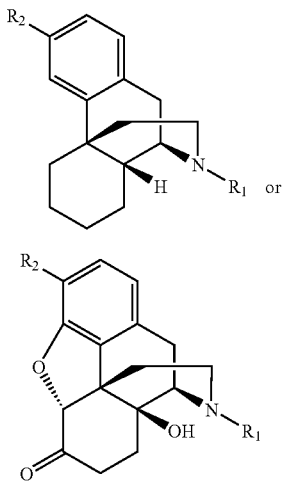

wherein $R_1$ is $C_{1-6}$ alkyl, $C_{2-6}$ alkenyl, cyclo$C_{3-6}$ alkyl-$C_{1-6}$ alkyl, or $C_{2-6}$ alkylene, $R_2$ is H, OH, $C_{1-6}$ alkyl, $C_{1-6}$ alkoxy, $C_{2-6}$ alkenyl or $C_{2-6}$ alkylene, and pharmaceutically acceptable carrier.

The composition of the present invention could be made in the form of tablet, capsule, gel cap, powder, solution, cream, ointment, lotion, mineral oil, or other things spread on epidermal or transdermal administration.

The examples below are non-limiting and are merely representative of various aspects and features of the present invention.

EXAMPLE

Example 1

Effect of Naloxone on Macrophage Activation

Materials

RPMI 1640 medium, phorbol 12-myristate-13-acetate (PMA), LPS (*Escherichia coli* 0111:B4) and naloxone were purchased from the Sigma-Aldrich (St. Louis, Mo., USA). The human THP-1 monocytic cell line was purchased from the Food Industry Research and Development Institute, Hsin Chu, Taiwan. Levels of tumor necrosis factor-α (TNF-α), interleukin-6 (IL-6) and monocyte chemoattractant protein-1 (MCP-1) in the medium or plasma were determined with monoclonal antibody based ELISA kits purchased from the R&D Systems (Minneapolis, Minn., USA). ApoE-deficient mice were obtained from the Jackson Laboratories (Bar Harbor, Me., USA). All animal experiments were approved by the Institutional Animal Care and Use Committee, National Cheng Kung University.

Pro-Inflammatory Factor and Superoxide in THP-1 Cell Culture

THP-1 cells were grown in the RPMI-1640 medium containing 10% fetal bovine serum at 37° C. in 5% $CO_2$. The cells were differentiated to macrophages after treatment of the culture with 100 nM PMA for 24 hours. The cell suspension ($5\times10^5$) was added in 0.5 mL into each well of the tissue culture plates. For each experiment, naloxone was prepared immediately before use. LPS was dissolved in sterile water and stored at −70° C. in aliquots. LDL was isolated from human endotoxin-free heparin plasma and was oxidized using $CuSO_4$. In brief, LDL (1 mL, 1 mg/mL) was dialyzed in 500 mL phosphate-buffered saline (PBS, pH 7.4) overnight. Copper sulfate was added to a final concentration of 5 μM, and the LDL was allowed to oxidize at room temperature for 24 hours.

First, we examined the effective naloxone concentration that inhibited TNF-α production from macrophages. Because a previous study (Liu B, Du L, Hong J S., J Pharmacol Exp Ther, 293:607-17, 2000) demonstrated that 1 μM naloxone could protect neurons through inhibition of microglia activation, our initial experiment began with this concentration. The THP-1 cell culture was pretreated for 1 hour with various concentrations of naloxone ($1$-$10^{-6}$ μM) prior to treatment with 100 ng/mL LPS for 24 hours. The TNF-α level in the supernatant was determined by ELISA. The most effective naloxone concentrations (1, 0.1, and 0.01 μM) were chosen for all the following experiments.

For study of pro-inflammatory factors, the THP-1 cell culture was pretreated for 1 hour with naloxone (1, 0.1, or 0.01 μM) prior to treatment with 100 ng/mL LPS or 10 μg/mL oxLDL for up to 24 hours. The supernatants were harvested and the TNF-α, IL-6, and MCP-1 levels were determined by ELISA. Superoxide production in the THP-1 cell culture was measured by lucigenin-enhanced chemiluminescence as described previously (Khadour F H, Panas D, Ferdinandy P, et al. Am J Physiol Heart Circ Physiol, 28:H1108-15 2002). LPS-treated THP-1 cells were treated with PBS containing 1.25 mM lucigenin, and counts were obtained for a 10-minute period in a luminometer (Berthold Technologies, Germany) as relative light units (RLU) emitted. Background counts determined in cell-free preparations were subtracted. Superoxide levels were reported as RLU per 10 minutes and were normalized to the volume (mL) of cell suspension added (i.e., RUL/10 min/mL).

Cell viability was determined with the 3 (4,5-dimethylthiazol-2-yl) 2,5-diphenyltetrazolium bromide (MTT) assay in each treatment group described above. Briefly, fresh medium was added to cells together with 10% MTT (5 mg/mL). Each plate was maintained at 37° C. for 2 hours and subsequently formazan crystals were dissolved in DMSO. Absorbance was read at a wavelength of 550 nm using a SPECTRAmax PLUS[384] spectrophotometer (Molecular Devices, CA, USA).

The initial experiment demonstrated that the most effective naloxone concentration range was 0.01-1 μM. These concentrations could reduce TNFα production by 50 percent in the THP1 cell culture after LPS stimulation (Table 1).

TABLE 1

Effect of naloxone pretreatment on inhibition of TNF-α production from the THP-1 cell culture after LPS stimulation

| Naloxone pretreatment μM | TNF-α production after LPS % control |
|---|---|
| 0 (control) | 100 ± 2 |
| 1 | 55 ± 2** |
| $10^{-1}$ | 51 ± 6** |
| $10^{-2}$ | 53 ± 6** |
| $10^{-3}$ | 67 ± 3** |
| $10^{-4}$ | 74 ± 7* |
| $10^{-5}$ | 93 ± 4 |
| $10^{-6}$ | 90 ± 10 |

TABLE 1-continued

Effect of naloxone pretreatment on inhibition of TNF-α production
from the THP-1 cell culture after LPS stimulation

| Naloxone pretreatment μM | TNF-α production after LPS % control |
|---|---|

Results are expressed as the percentage of the control group and are the mean ± SD of three or four experiments. The value for control was 8.02 ± 0.42 ng/mL.
*P < 0.05;
**P < 0.01 compared with the control group.
LPS, lipopolysaccharide;
TNF-α, tumor necrosis factor-α.

Figure 1:
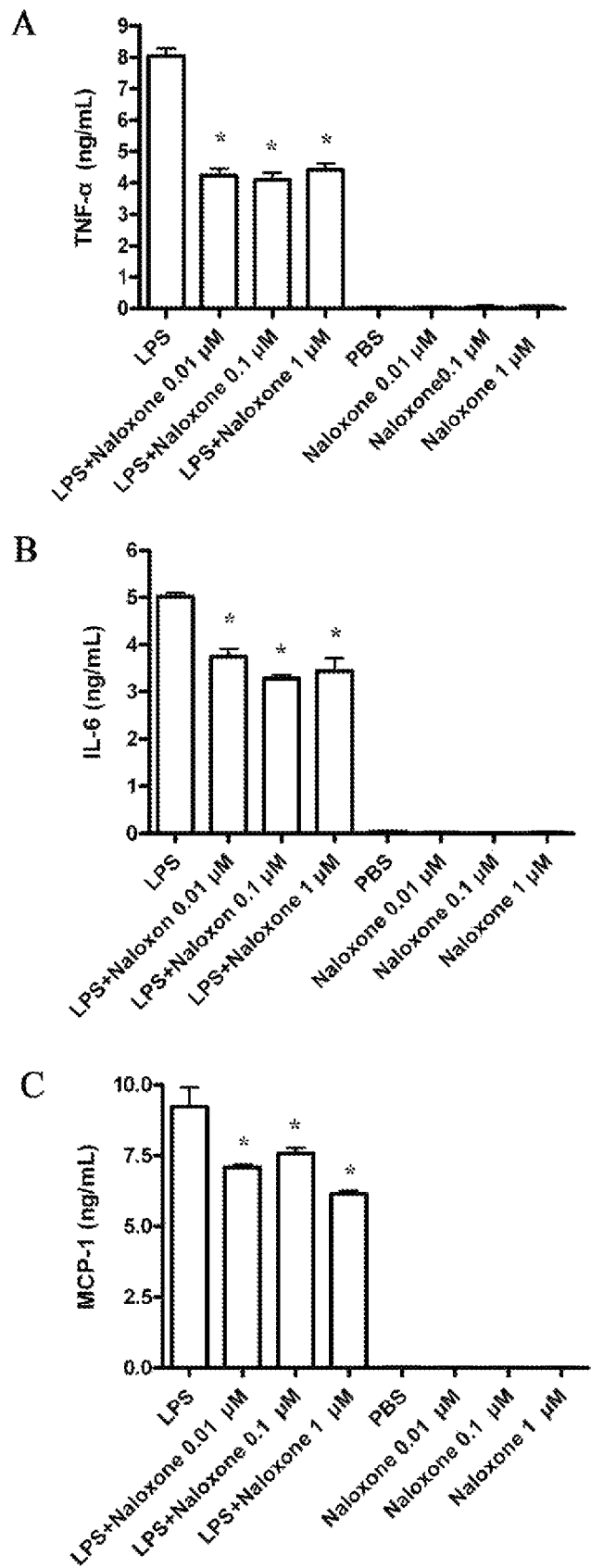
FIG. 1 shows effect of naloxone treatment on the LPS-induced macrophage release of TNF-α (A), IL-6 (B) and MCP-1 (C). THP-1 cell culture was pretreated for 1 hour with the indicated concentrations of naloxone before stimulation with 100 ng/mL LPS. Supernatants were harvested at 24 hours for the measurement of TNF-α, IL-6 and MCP-1. The results are expressed as mean±SD of 3 experiments. *$P<0.05$ compared with the LPS-treated cultures.

Subsequent experiments were performed with these effective naloxone concentrations. LPS treatment induced a dramatic increase of TNFα (8.02±0.42 ng/mL), IL-6 (5.02±0.14 ng/mL), and MCP-1 (9.22±1.17 ng/mL) in the medium of the THP-1 cell culture when compared with the PBS treatment (TNFα 0.02±0.02 ng/mL, IL-6 0.03±0.02 ng/mL, MCP-1 0.03±0.04 ng/mL). Naloxone pretreatment (0.01, 0.1, and 1 μM) significantly reduced the macrophage production of TNFα (0.01 μM, 4.28±0.39 ng/mL; 0.1 μM, 4.10±0.37 ng/mL; 1 μM, 4.41±0.36 ng/mL vs 8.02±0.42 ng/mL, all P<0.05), IL-6 (0.01 μM, 3.74±0.31 ng/mL; 0.1 μM, 3.28±0.14 ng/mL; 1 μM, 3.44±0.48 ng/mL vs 5.02±0.14 ng/mL, all P<0.05) and MCP-1 (0.01 μM, 7.08±0.16 ng/mL; 0.1 μM, 7.32±0.33 ng/mL; 1 μM, 6.16±0.16 ng/mL vs 9.22±1.17 ng/mL, all P<0.05) in the medium of THP-1 cells after LPS stimulation (FIG. 1).

Figure 2:
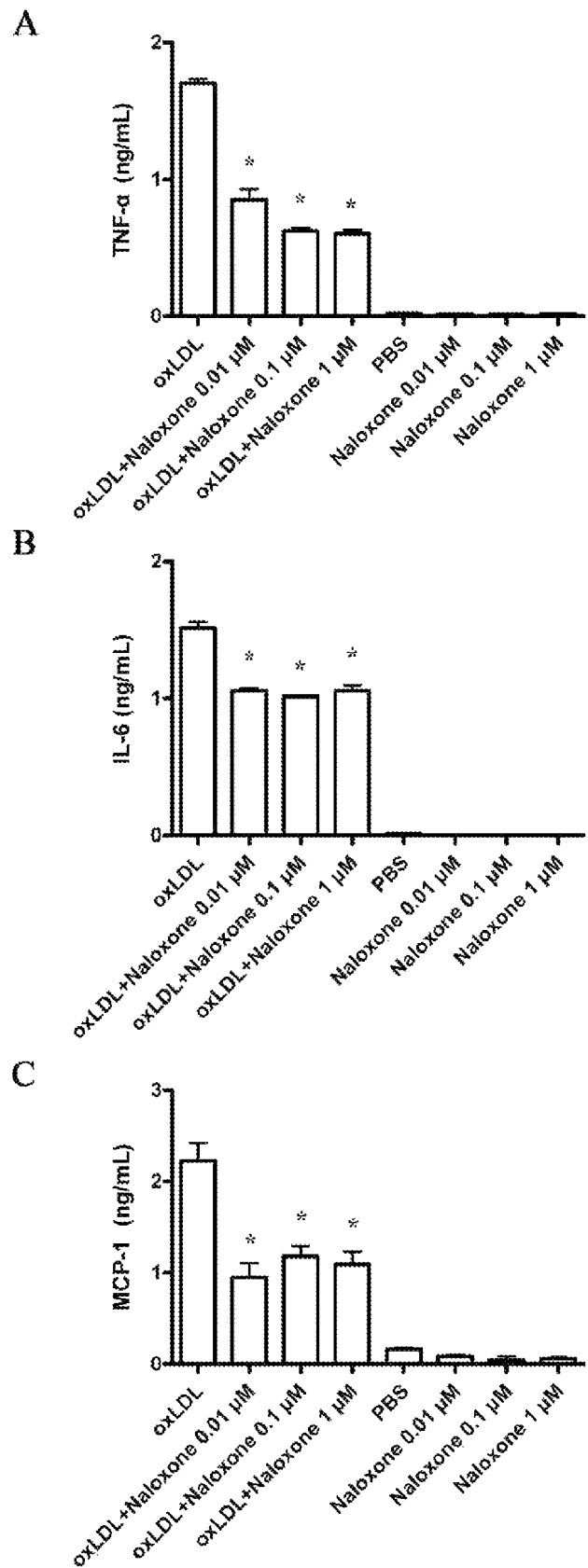
FIG. 2 shows effect of naloxone treatment on oxLDL-induced macrophage release of TNF-α (A), IL-6 (B) and MCP-1 (C). THP-1 cell culture was pretreated for 1 hour with the indicated concentrations of naloxone before stimulation with 10 μg/mL oxLDL. Supernatants were harvested at 24 hours for the measurement of TNF-α, IL-6 and MCP-1. The results are expressed as mean±SD of 3 experiments. *$P<0.05$ compared with the oxLDL-treated cultures.

After oxLDL stimulation, there was also a dramatic increase of TNFα (1.70±0.06 ng/mL), IL-6 (1.51±0.08 ng/mL) and MCP-1 (2.23±0.34 ng/mL) in the medium of the THP-1 cell culture when compared with the PBS treatment (TNFα 0.02±0.01 ng/mL, IL-6 0.01±0.01 ng/mL, MCP-1 0.16±0.03 ng/mL). Naloxone pretreatment (0.01, 0.1, and 1 μM) significantly reduced the macrophage production of TNFα (0.01 μM, 0.85±0.12 ng/mL; 0.1 μM, 0.62±0.04 ng/mL; 1 μM, 0.60±0.05 ng/mL; vs 1.70±0.06 ng/mL, all P<0.05), IL-6 (0.01 μM, 1.05±0.03 ng/mL; 0.1 μM, 1.01±0.01 ng/mL; 1 μM, 1.05±0.07 ng/mL vs 1.51±0.08 ng/mL, all P<0.05) and MCP-1 (0.01 μM, 0.95±0.28 ng/mL; 0.1 μM, 1.18±0.19 ng/mL; 1 μM, 1.09±0.24 ng/mL vs 2.23±0.34 ng/mL, all P<0.05) in the medium of THP-1 cells after oxLDL stimulation (FIG. 2).

Figure 3:
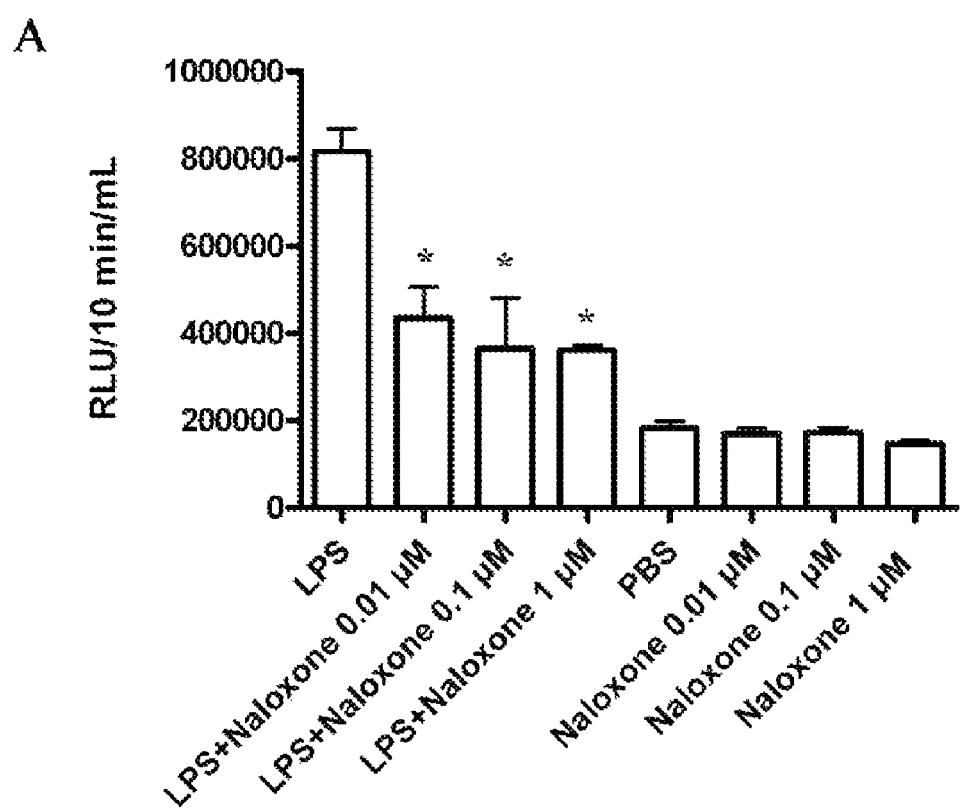
FIG. 3 shows effect of naloxone treatment on LPS-induced macrophage production of superoxide. THP-1 cell culture was pretreated for 1 hour with the indicated concentrations of naloxone before stimulation with 100 ng/mL LPS. Production of superoxide in THP-1 cell culture was measured by lucigenin-enhanced chemiluminescence. Data are expressed as the mean±SD of 3 experiments. *$P<0.05$ compared with the LPS-treated cultures.

FIG. 3 shows the production of superoxide in the THP-1 cell culture in the different treatment groups. Superoxide production was significantly increased after LPS stimulation (817,000±90,000 RLU/10 min/mL) when compared with the control group treated with only PBS (183,000±39,000 RLU/10 min/mL). Naloxone pretreatment (0.01, 0.1, and 1 μM) significantly suppressed the elevation of macrophage superoxide production (0.01 μM, 434,000±124,000 RLU/10 min/mL; 0.1 μM, 364,000±202,000 RLU/10 min/mL; 1 μM, 362,000±24,000 RLU/10 min/mL vs 817,000±90,000 RLU/10 min/mL, all P<0.05). MTT assays demonstrated that there were no significant changes of the cell viability between the THP-1 cell cultures receiving PBS, LPS, 0.01, 0.1, or 1 μM naloxone or LPS plus 0.01, 0.1, or 1 μM naloxone pretreatment.

Example 2

Effect of Naloxone on TNF-α and Superoxide Production in Mice

Pro-Inflammatory Factor and Superoxide Production in Mice

The anti-inflammatory effect of naloxone in adult male FVB mice (8-12 weeks old) was examined. The mice received pretreatment with intraperitoneal naloxone (10, 20, or 25 mg/kg) or PBS 30 minutes before the experiment. All mice then received 20 mg/kg LPS by intraperitoneal injection. Blood samples were obtained at 6 hours after LPS injection from a catheter placed in the left carotid artery. Blood samples were centrifuged, and the plasma TNF-α levels were measured by ELISA. Lungs were harvested from the animals 6 hours after LPS injection in each group as described above. The tissues were fixed in 4% paraformaldehyde and embedded in paraffin for histopathological examination. The presence of inflammatory cells in lungs was determined by immunofluorescence. The sections were incubated with rat monoclonal antibody against mouse CD45, a leukocyte common antigen (1:50 dilution, Pharmingen). After washing, fluorescein isothiocyanate-conjugated sheep anti-mouse immunoglobulin (Amersham Pharmacia Biotech) was applied as a secondary antibody. A laser scanning confocal microscope (Leica Microsystems, Germany) was used to examine the samples and the CD45-positive cells were demonstrated by green immunofluorescence labeling. The total CD45-positive cell number was counted in five randomly selected sections under high power field magnification (400×) for each mouse. Oxidative fluorescent microtopography with the oxidative fluorescent dye dihydroethidium (DHE) was used to evaluate the in situ production of superoxide in aorta. Aortas were harvested from the animals at 6 hours after LPS injection in each group as described above. Unfixed frozen ring segments were cut into 30-μm-thick sections and placed on a glass slide. DHE (10 μM) was topically applied to each tissue section and a cover slip was applied. Slides were incubated in a light-protected humidified chamber at 37° C. for 30 minutes. Fluorescence was detected with a laser scanning confocal microscope (Leica Microsystems, Germany) with excitation at 488-nm and detection at 585-nm using a long-pass filter.

Naloxone Treatment in apoE-Deficient Mice

ApoE-deficient mice were fed with a high cholesterol diet containing 21% fat and 0.15% cholesterol (PMI LabDiet 40097, Richmond, Ind., USA) from 8-17 weeks of age. The apoE-deficient mice received intraperitoneal naloxone (10, 20, or 25 mg/kg/day) or PBS injection for 10 weeks during this period. After completing the treatment, blood samples were collected by direct heart puncture when sacrificing the animals. The serum levels of total cholesterol, LDL, HDL, and triglyceride were measured by enzymatic methods using an automatic analyzer (Model 747, Hitachi Ltd. Co., Tokyo, Japan). The aorta was dissected from the aortic valve to the iliac bifurcation. To identify lipid-rich atherosclerotic lesions, the aorta was rinsed in 50% isopropanol for 2 minutes, incubated in 0.67% Oil-Red-O for 15 minutes, and washed by 10% isopropanol for 2 minutes. Using a dissection microscope, the area of each atherosclerotic lesion was measured with Image Pro Plus software (Version 3.0.1; Media Cybernetics, Inc, Silver Spring, Md., USA) and expressed as percentage of atherosclerotic area/total area of the aorta.

Figure 4:
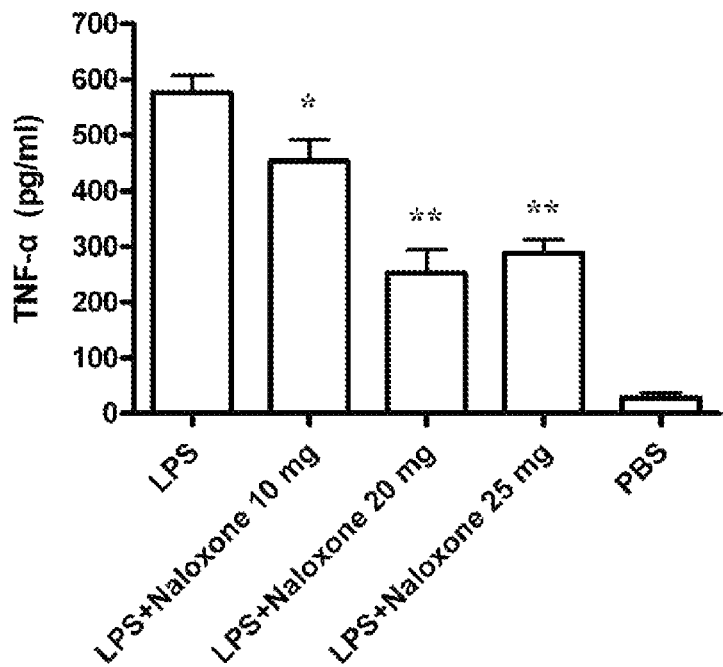
FIG. 4 shows effect of naloxone treatment on the plasma levels of TNF-α (A) and the pulmonary inflammatory cell (CD 45 positive cells) infiltration (B) in mice. (A) Mice were pretreated with the indicated dose of naloxone (n=8 in 10 mg/kg, n=7 in 20 mg/kg and n=5 in 25 mg/kg naloxone) or PBS (n=7) before stimulation with LPS. Plasma TNF-α levels were measured by ELISA. Data are expressed as the mean±SD. *$P<0.05$; $P<0.01$ compared with the LPS-treated only group (n=9). (B) Mice were pretreated with the indicated dose of naloxone (n=5 in 10 mg/kg, n=6 in 20 mg/kg and n=5 in 25 mg/kg naloxone) or PBS (n=9) before stimulation with LPS. The presence of inflammatory cells in lungs was determined by immunofluorescence. Data are expressed as the mean±SD. $P<0.01$ compared with the LPS-treated only group (n=7).
Figure 4:
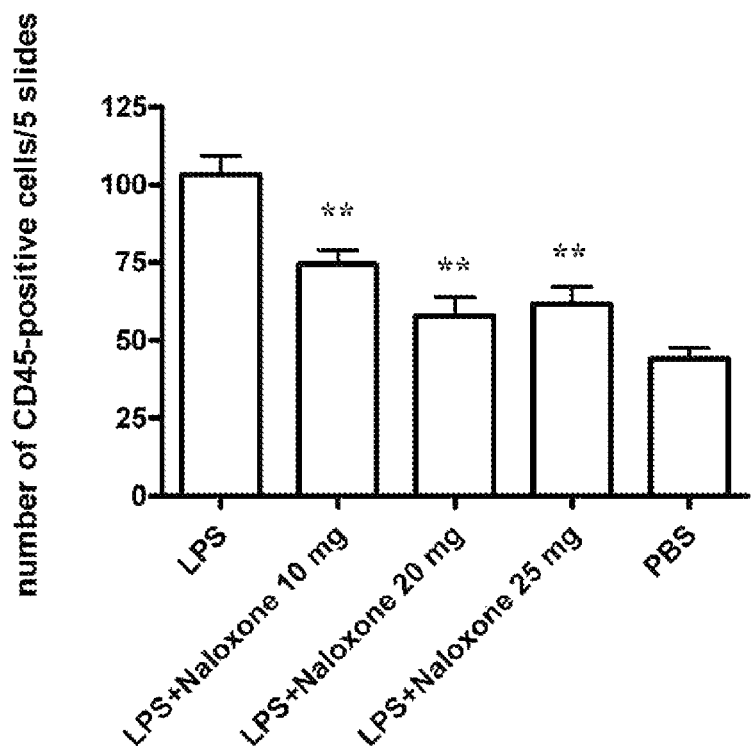
Figure 5:
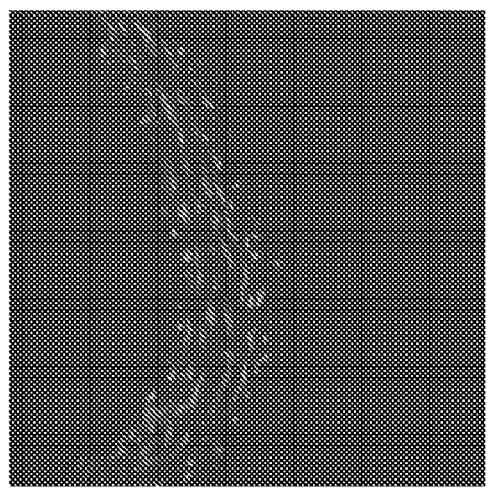
FIG. 5 shows superoxide formation in the mouse aorta evaluated by oxidative fluorescent microtopography with the oxidative fluorescent dye DHE. Representative photomicrographs of the aortic sections in mice receiving LPS (A), 20 mg/kg naloxone pretreatment 1 hour before LPS (B), and PBS (C) are shown. Increased superoxide production was visualized by amplified red fluorescence in the aortic wall after LPS stimulation (A). In comparison, staining was much more reduced in the aorta of animals receiving naloxone pretreatment (B). (bar=50 μm)
Figure 5:
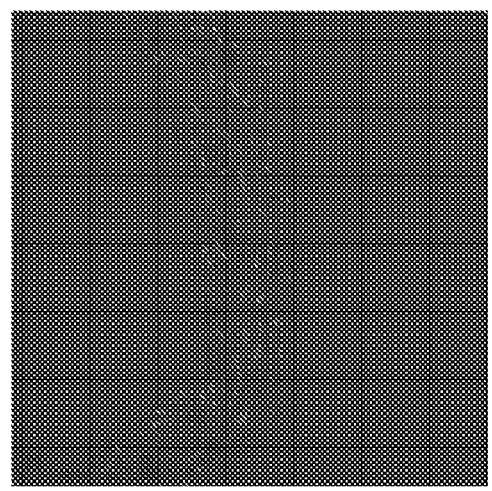
Figure 5:
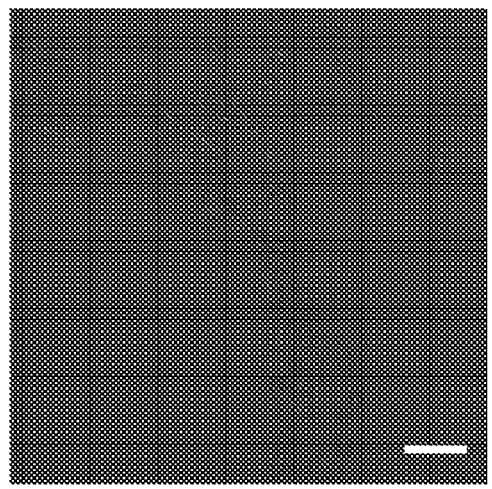

FIG. 4 shows the effect of naloxone on the TNF-α and superoxide production in the mice after stimulation. The plasma level of TNF-α was significantly elevated in the LPS-treated (n=9) compared with the PBS-treated (n=7) mice (576.1±43.6 vs 27.8±13.1 pg/mL, P<0.001). Pretreatment of the mice with naloxone (n=8 in 10 mg/kg, n=7 in 20 mg/kg, and n=5 in 25 mg/kg naloxone) effectively reduced the elevation of the plasma TNF-α levels (10 mg/kg, 452.9±55.0 pg/mL, P<0.05; 20 mg/kg, 251.9±59.6 pg/mL, p<0.01; 25 mg/kg, 288.0±33.9 pg/mL, P<0.01 vs 576.1±43.6 pg/mL). There was more pulmonary inflammatory cell infiltration in the mice after LPS stimulation (n=7) compared with PBS injection only (n=9; 103±16 vs 45±10, P<0.01). In the mice pretreated with naloxone (n=5 in 10 mg/kg, n=6 in 20 mg/kg, and n=5 in 25 mg/kg naloxone), the infiltration of inflammatory cells in the lungs was significantly decreased (10 mg/kg, 74±10; 20 mg/kg, 58±15; 25 mg/kg, 62±12, all P<0.01 vs 103±16). Aortic sections from the mice were stained with DHE and then imaged with a laser scanning confocal microscope. The LPS-treated mice showed a marked increase in fluorescence, reflecting an increase in superoxide production in aorta (FIG. 5). Naloxone pretreatment (10, 20, and 25 mg/kg) significantly reduced the increase of fluorescence intensity in the aortic sections from the LPS-treated mice.

Example 3

Effect of Naloxone on Atherosclerosis and Neointima Formation

Effect of Naloxone Treatment in a Mouse Vascular Remodeling Model

Adult C57BL/6 mice (8-12 weeks) were anesthetized by intraperitoneal injection of sodium pentobarbital. The left common carotid artery was isolated and ligated completely with a 6-0 silk suture near the carotid bifurcation. The mice received intraperitoneal naloxone (10, 20, or mg/kg/day) or PBS injection for 4 weeks immediately after surgery. After completing the treatment the animals were sacrificed and the segment of the left common carotid artery just proximal to the ligation was excised, fixed in 4% paraformaldehyde, and embedded in paraffin. Five transverse sections per animal were cut at 100 μm intervals and stained with hematoxylin-eosin. The borders of the internal lumen, internal elastic lamina (IEL), and external elastic lamina (EEL) were traced on a digitizing board using Meta Imaging Series 5.0 software (Adobe Inc.). The luminal, IEL, and EEL areas were measured. The neointima area was calculated by subtracting the luminal area from the IEL area, and the media area was calculated by subtracting the IEL area from the EEL area. The total vascular area was represented by EEL area. The ratio of neointima to media area (N/M ratio) was calculated. Average values were obtained from morphometric analysis of each section of the animal.

Statistical Analyses

Data were given as mean±SD. The Mann-Whitney U test was used to compare continuous variables between the two groups. Because there was a tremendous variability of vascular remodeling along the ligated carotid artery, and the distance to the ligation site may influence the thickness of neointima formation, multiple regression analysis was performed to simultaneously analyze the contribution of the distance to ligation site and naloxone treatment on the response of carotid ligation (Myers D L, Liaw L. Improved analysis of the vascular response to arterial ligation using a multivariate approach. Am J Pathol 2004; 164:43-8). All statistical analyses were performed using SPSS 12.0 (SPSS Inc. Chicago, Ill., USA). The statistical significance level was set at P<0.05, two-tailed.

Figure 6:
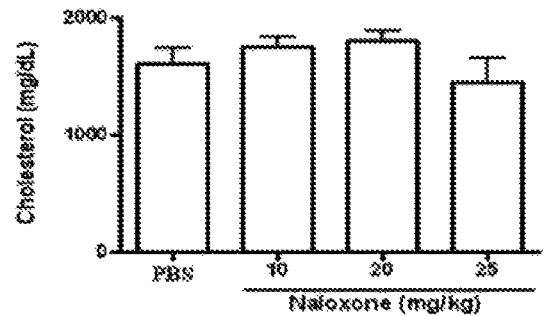
FIG. 6 shows influence of naloxone treatment on the plasma levels of cholesterol (A), triglyceride (B), LDL (C), and HDL (D). ApoE-deficient mice received intraperitoneal injection of PBS (n=8), 10 mg/kg/day (n=8), 20 mg/kg/day (n=7) or 25 mg/kg/day (n=5) naloxone for 10 weeks. The results are expressed as mean±SD.
Figure 6:
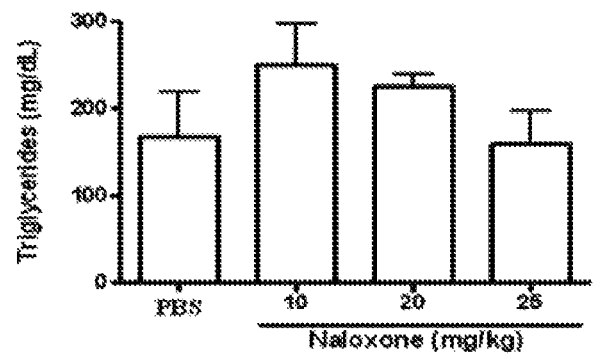
Figure 6:
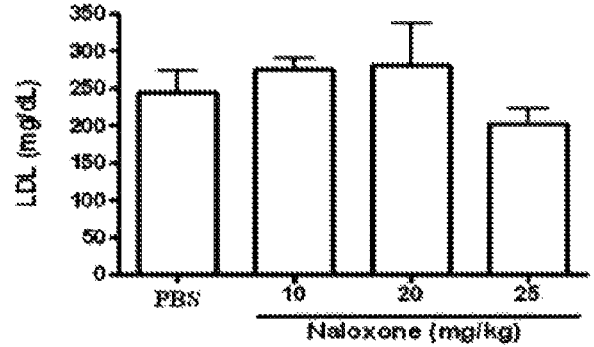
Figure 6:
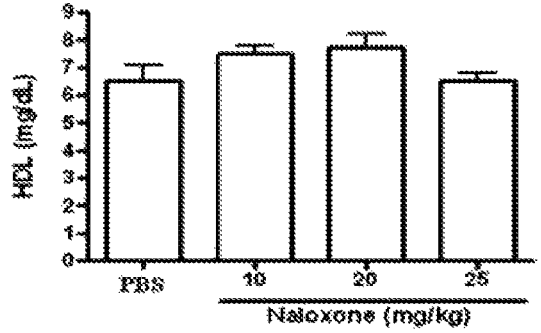
Figure 7:
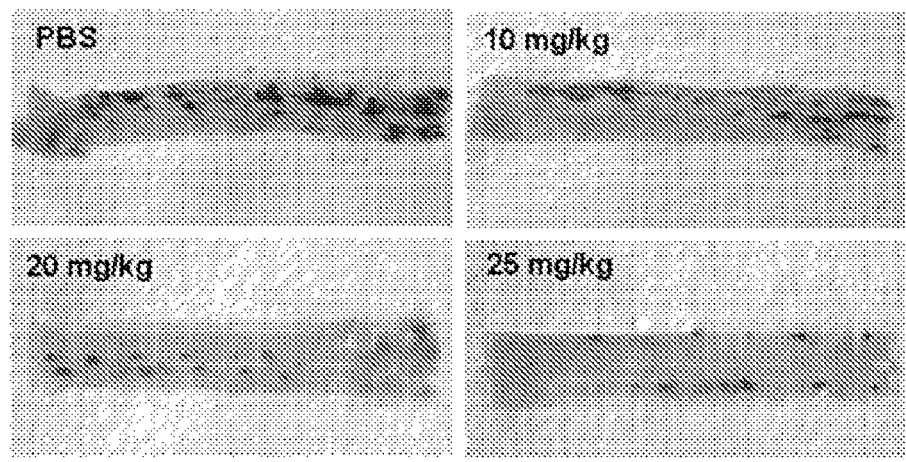
FIG. 7 shows influence of naloxone treatment on atherosclerotic lesion formation in apoE-deficient mice (A). The lipid-rich atherosclerotic lesions were identified with Oil-Red-O staining. Lesion area (%) was expressed as percentage of atherosclerotic area/total area of the aorta (B). ApoE-deficient mice received intraperitoneal injection of PBS (n=8), 10 mg/kg/day (n=8), 20 mg/kg/day (n=7) or 25 mg/kg/day (n=5)
Figure 7:
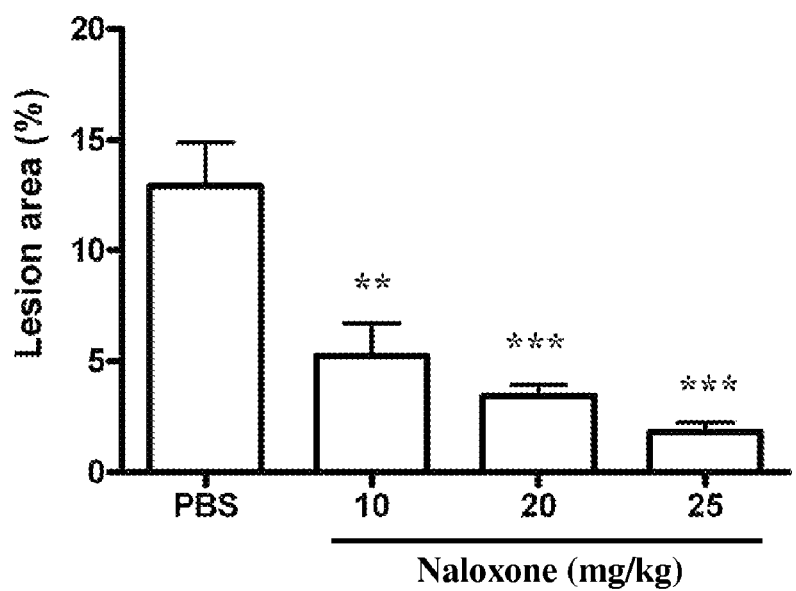

The apoE-deficient mice received intraperitoneal naloxone (n=7 in 10 mg/kg, n=9 in 20 mg/kg, and n=8 in 25 mg/kg naloxone) or PBS (n=10) injection for 10 weeks. There were no significant differences of the total cholesterol, triglyceride, LDL, and HDL levels between the PBS and naloxone-treatment groups (FIG. 6). Naloxone treatment for 10 weeks significantly reduced the severity of aortic atherosclerotic lesions (10 mg/kg/day, 5.2±3.8%, P<0.01; 20 mg/kg/day, 3.4±1.4%, P<0.005; 25 mg/kg/day, 1.8±1.2%, P<0.005 vs PBS 12.9±6.1%) in the apoE-deficient mice (FIG. 7).

There was a progressively decreased lumen area and increased neointima formation in C57BL/6 mice after carotid artery ligation (FIG. 8). The lumen area was significantly larger (10 mg/kg/day, 24475±5261 μm$^2$; 20 mg/kg/day, 26452±9024 μm$^2$; 25 mg/kg/day, 29650±5643 μm$^2$, all P<0.05 vs PBS 12859±7258 μm$^2$) at 28 days in mice receiving naloxone treatment (n=5 in 10, n=7 in 20 and n=5 in 25 mg/kg/day) compared with the controls receiving PBS only (n=7). The neointima area was significantly reduced (10 mg/kg/day, 20052±4372 μm$^2$, P<0.01; 20 mg/kg/day, 14233±4040 μm$^2$, P<0.005; 25 mg/kg/day, 13865±3494 μm$^2$, P<0.005 vs PBS 33623±9377 μm$^2$) after naloxone treatment. The N/M ratio was also decreased in naloxone-treatment group (10 mg/kg/day, 0.66±0.15; 20 mg/kg/day, 0.41±0.18; 25 mg/kg/day, 0.39±0.07, all P<0.005 vs PBS 1.25±0.42) at 28 days after surgery (FIG. 8). In the regression model (Table 2), naloxone treatment had a statistically significant influence on the lumen, neointima, and total vascular areas in carotid remodeling after ligation, and the effect was independent of the distance to ligation.

TABLE 2

Regression model of carotid ligation response in mice receiving naloxone or saline treatment.

|  | | Distance to ligation |
| --- | --- | --- |
| | Naloxone (10 mg/kg/day) | |
| Lumen area | | |
| coefficient | 12016 | 1806 |
| p value | <0.001 | 0.857 |
| Neointima area | | |
| coefficient | −13951 | −4628 |
| p value | <0.001 | 0.657 |
| Media area | | |
| coefficient | 2950 | −4288 |
| p value | 0.176 | 0.574 |
| Total area | | |
| coefficient | −11000 | −8916 |
| p value | 0.007 | 0.519 |
| | Naloxone (20 mg/kg/day) | |
| Lumen area | | |
| coefficient | 14033 | 12073 |
| p value | <0.001 | 0.276 |
| Neointima area | | |
| coefficient | −19584 | −21986 |
| p value | <0.001 | 0.023 |
| Media area | | |
| coefficient | 10001 | −4685 |
| p value | 0.001 | 0.645 |
| Total area | | |
| coefficient | −9582 | −26672 |
| p value | 0.012 | 0.046 |

TABLE 2-continued

Regression model of carotid ligation response in mice receiving naloxone or saline treatment.

|  | Naloxone (25 mg/kg/day) | Distance to ligation |
|---|---|---|
| Lumen area | | |
| coefficient | 16993 | 20041 |
| p value | <0.001 | 0.06 |
| Neointima area | | |
| coefficient | −20380 | −5073 |
| p value | <0.001 | 0.619 |
| Media area | | |
| coefficient | 8112 | −30696 |
| p value | 0.015 | 0.009 |
| Total area | | |
| coefficient | −12267 | −35770 |
| p value | 0.01 | 0.033 |

Area = B1 + B2 (Naloxone) + B3 (Distance (mm))

Example 4

Dextromethorphan Treatment Reduced Macrophage Cytokine Production

To investigate the DM effect on macrophage activation, determined the effective DM concentrations were first needed. In a pilot experiment, the effective DM concentration that inhibited TNF-α production from macrophages was examined. Because the previous study (Liu, Y., Qin, L., Li, G., Zhang, W., An, L., Liu, B., and Hong, J. J. Pharmacol. Exp. Ther. 305:212-218, 2003) demonstrated that 1 μM DM could inhibit microglia activation, our initial experiment began with this concentration. The THP-1 cell culture was pretreated for 1 hour with various concentrations of DM ($1$-$10^{-8}$ μM) prior to treatment with 100 ng/mL LPS for 24 hours. The TNF-α level in the supernatant was determined by ELISA. The initial experiment demonstrated that the most effective DM concentrations that suppressed macrophage TNF-α production after LPS stimulation was 0.01-1 μM. One μM DM could reduce TNF-α production up to 44 percent in the THP-1 cell culture after LPS stimulation (Table 3). Therefore, subsequent experiments were performed with these effective DM concentrations (0.01, 0.1, and 1 μM).

TABLE 3

Effect of DM pretreatment on inhibition of TNF-α production from the THP-1 cell culture after LPS stimulation

| DM pretreatment μM | TNF-α production after LPS % control |
|---|---|
| 0 (control) | 100 ± 2 |
| 1 | 56 ± 10** |
| $10^{-1}$ | 72 ± 2** |
| $10^{-2}$ | 74 ± 4** |
| $10^{-4}$ | 81 ± 9* |
| $10^{-6}$ | 83 ± 3* |
| $10^{-8}$ | 95 ± 7 |

Results are expressed as the percentage of the control group and are the mean ± SD of three or four experiments. The value for control was 8.13 ± 0.38 ng/mL.
*P < 0.05;
**P < 0.01 compared with the control group.

We first explored the DM effect on macrophage cytokine production after LPS and oxLDL stimulation. LPS treatment induced a dramatic increase of TNF-α (8.85±0.81 ng/mL) and IL-6 (9.53±1.95 ng/mL) in the medium of the THP-1 cell culture when compared with the PBS treatment (TNF-α 0.14±0.05 ng/mL, IL-6 0.06±0.03 ng/mL). DM pretreatment (0.01, 0.1, and μM) of the THP-1 cell culture significantly reduced the macrophage production of TNF-α (0.01 μM, 6.93±0.76 ng/mL; 0.1 μM, 6.42±0.73 ng/mL; 1 μM, 5.85±1.12 ng/mL vs 8.85±0.81 ng/mL, all P<0.001) and IL-6 (0.01 μM, 6.22±2.46 ng/mL; 0.1 μM, 6.21±1.89 ng/mL, P<0.05; 1 μM, 5.36±1.76 ng/mL, P<0.01 vs 9.53±1.95 ng/mL) in the medium of THP-1 cells after LPS stimulation (FIG. 9). The similar DM effect was observed in oxLDL experiment. After oxLDL stimulation, there was also a dramatic increase of TNF-α (2.64±0.61 ng/mL) and IL-6 (2.46±1.20 ng/mL) in the medium of the THP-1 cell culture when compared with the PBS treatment (TNF-α 0.05±0.03 ng/mL, IL-6 0.04±0.03 ng/mL). DM pretreatment (0.01, 0.1, and 1 μM) significantly reduced the macrophage production of TNF-α (0.01 μM, 1.80±0.53 ng/mL, P<0.05; 0.1 μM, 1.75±0.33 ng/mL; 1 μM, 1.77±0.42 ng/mL, P<0.01 vs 2.64±0.61 ng/mL) and IL-6 (0.01 μM, 1.40±0.58 ng/mL; 0.1 μM, 1.28±0.64 ng/mL; 1 μM, 1.33±0.67 ng/mL vs 2.46±1.20 ng/mL, all P<0.05) in the medium of THP-1 cells after oxLDL stimulation (FIG. 10).

Example 5

Dextromethorphan Treatment Reduced Macrophage Superoxide Production

We used lucigenin-enhanced chemiluminescence to assess the DM effect on macrophage superoxide production after stimulation. FIG. 11 shows the production of superoxide in the THP-1 cell culture in different treatment groups. Superoxide production in the THP-1 cells was significantly increased after LPS stimulation (612,000±105,000 RLU/15 min/mL) when compared with the control group treated with only PBS (128,000±29,000 RLU/15 min/mL). DM pretreatment (0.01, 0.1, and 1 μM) significantly suppressed the elevation of macrophage superoxide production (0.01 μM, 341,000±82,000 RLU/15 min/mL; 0.1 μM, 303,000±109,000 RLU/15 min/mL; 1 μM, 257,000±45,000 RLU/15 min/mL vs 612,000±105,000 RLU/15 min/mL, all P<0.001) after LPS stimulation. MTT assays demonstrated that there were no significant changes of the cell viability between the THP-1 cell cultures receiving PBS, LPS, 0.01, 0.1, or 1 μM DM or LPS plus 0.01, 0.1, or 1 μM DM pretreatment.

Example 6

Dextromethorphan Treatment Reduced Macrophage NADPH Oxidase Activity

Given that the DM anti-inflammatory effect was not observed in NADPH oxidase-deficient mice (Zhang, W., Wang, T., Qin, L., Gao, H. M., Wilson, B., Ali, S. E, Zhang, W., Hong, J. S., and Liu, B. FASEB. J. 18:589-591, 2004), lucigenin-enhanced chemiluminescence was used to examine whether DM could directly inhibit the macrophage NADPH oxidase activity. FIG. 12 shows the macrophage NADPH oxidase activity in different treatment groups. Macrophage NADPH oxidase activity was significantly increased after LPS stimulation (3,310,000±1,670,000 RLU/15 min/mL) when compared with the control group treated with only PBS (780,000±410,000 RLU/15 min/mL). DM pretreatment (0.01, 0.1, and 1 µM) significantly inhibited the NADPH oxidase activity (0.01 µM, 1,360,000±860,000 RLU/15 min/mL; 0.1 µM, 1,280,000±540,000 RLU/15 min/mL; 1 µM, 1,400,000±730,000 RLU/15 min/mL vs 3,310,000±1,670,000 RLU/15 min/mL, all P<0.001) after LPS stimulation.

Example 7

Dextromethorphan Treatment Reduced Superoxide Production in Mice

Having established the DM inhibitory effect on macrophage activation and NADPH oxidase, we next examined the functional consequences of which in vivo. FIG. 13A shows the effect of DM on the superoxide production in the apoE-deficient mice. Pretreatment of the mice with 10, 20 or 40 mg/kg/day DM for 10 weeks effectively reduced the PMN production of superoxide (5 mg/kg/day, 460,000±138,000 RLU/15 min, P=NS; 10 mg/kg/day, 390,000±63,000 RLU/15 min, P<0.05; 20 mg/kg/day, 328,000±82,000 RLU/15 min; 40 mg/kg/day, 328,000±82,000 RLU/15 min, P<0.001 vs controls 519,000±115,000 RLU/15 min) (FIG. 13A). The superoxide in the thoracic aorta was also significantly reduced in these mice pretreated with DM (5 mg/kg, 424,000±141,000 RLU/15 min, P=NS; 10 mg/kg, 377,000±97,000 RLU/15 min, P<0.05; 20 mg/kg, 341,000±94,000 RLU/15 min, P<0.01; 40 mg/kg, 379,000±84,000 RLU/15 min, P<0.05 vs controls 534,000±145,000 RLU/15 min) (FIG. 13B). Sections of left carotid arteries from the mice were stained with DHE and then imaged with a laser scanning confocal microscope. The apoE-deficient mice showed a marked increase in fluorescence, reflecting an increase in superoxide production in the artery (FIG. 14). DM pretreatment (10, 20, and 40 mg/kg/day) for 10 weeks significantly reduced the increase of fluorescence intensity in the sections of left carotid arteries indicating the decrease of superoxide production in the arteries of the mice.

Example 8

Dextromethorphan Treatment Inhibited Atherosclerosis and Neointima Formation

The findings of our previous experiments raised the possibility that DM treatment might influence atherosclerosis through the inhibitory effect on inflammation and superoxide production. Thus, we used two animal models, apoE-deficient mice and carotid ligation model, to study the DM effect. There were no significant differences of the total cholesterol, triglyceride, LDL, and HDL levels between the apoE-deficient mice receiving DM treatment for 10 weeks and the controls. DM treatment (10, 20 and 40 mg/kg/day) for 10 weeks significantly reduced the severity of aortic atherosclerotic lesions (5 mg/kg/day, 14.1±5.7%, P=NS; 10 mg/kg/day, 8.2±3.8%; 20 mg/kg/day, 5.0±2.0%; 40 mg/kg/day, 4.6±3.6%, all P<0.001 vs controls 16.9±4.3%) in the apoE-deficient mice (FIG. 15). There was a progressively decreased lumen area and increased neointima formation in C57BL/6 mice after carotid artery ligation for 4 weeks (FIG. 16). The neointima/media (N/M) ratio was decreased in the DM treatment group (5 mg/kg/day, 1.1±0.7, P=NS; 10 mg/kg/day, 0.7±0.3, P<0.01; 20 mg/kg/day, 0.4±0.2; 40 mg/kg/day, 0.5±0.2, P<0.001 vs controls 1.4±0.6) at 28 days after surgery indicating DM treatment for 4 weeks significantly reduced the severity of neointima formation in the mice.

What is claimed is:

1. A method for treating in-stent restenosis comprising administering to a patient in need of such treatment a therapeutically effective amount of only one compound of (+)-3-methoxy-17-methyl-9α,13α,14α-morphinan (dextromethorphan), 17-allyl-4,5α-epoxy-3,14-dihydroxymorphinan-6-one (naloxone), or 17-(cyclopropylmethyl)-4,5α-epoxy-3,14-dihydroxymorphinan-6-one (naltrexone), or a pharmaceutically acceptable salt thereof.

2. The method of claim 1, wherein the salt is dextromethorphan hydrobromide or dextromethorphan phosphate.

3. The method of claim 1 wherein the method consists of only the administering step of said compound, and wherein said compound is administered alone without other compounds.

4. The method of claim 3 wherein the compound is said naloxone having a concentration of 0.01 to 1 µM.

5. The method of claim 3 wherein the compound is said naloxone using a dosage range from 10 mg/kg/day to 25 mg/kg/day.

6. The method of claim 3 wherein the compound is said Dextromethorphan having a concentration of 0.01 to 1 µM.

7. The method of claim 3 wherein the compound is said Dextromethorphan using a dosage range from 5 mg/kg/day to 40 mg/kg/day.

8. A method for treating atherosclerosis comprising administering a patient in need of such treatment a therapeutically effective amount of only one compound of
   a) (+)-3-methoxy-17-methyl-9α,13α,14α-morphinan (dextromethorphan),
   b) 17-allyl-4,5α-epoxy-3,14-dihydroxymorphinan-6-one (naloxone), and
   c) 17-(cyclopropylmethyl)-4,5α-epoxy-3,14-dihydroxymorphinan-6-one (naltrexone),
or a pharmaceutically acceptable salt or an analog thereof.

9. The method of claim 8, wherein the salt is dextromethorphan hydrobromide or dextromethorphan phosphate.

10. The method of claim 8 wherein the compound is said naloxone having a concentration of 0.01 to 1 µM.

11. The method of claim 8 wherein the compound is said naloxone using a dosage range from 10 mg/kg/day to 25 mg/kg/day.

12. The method of claim 8 wherein the compound is said Dextromethorphan having a concentration of 0.01 to 1 µM.

13. The method of claim 8 wherein the compound is said Dextromethorphan using a dosage range from 5 mg/kg/day to 40 mg/kg/day.

* * * * *